US005118502A

United States Patent [19]

[11] Patent Number: 5,118,502

Glisson et al.

[45] Date of Patent: Jun. 2, 1992

[54] NATURALLY ATTENUATED NEWCASTLE DISEASE VACCINE AND METHOD OF USING THE SAME

[75] Inventors: John R. Glisson; Pedro Villegas, both of Athens, Ga.

[73] Assignee: The University of Georgia Research Foundation, Inc., Athens, Ga.

[21] Appl. No.: 369,071

[22] Filed: Jun. 20, 1989

[51] Int. Cl.[5] .......................... A61K 39/12; C12N 7/00

[52] U.S. Cl. .................................... 424/89; 435/235.1; 435/236; 435/237; 435/239; 435/240.1; 435/245
[58] Field of Search ............... 424/89; 435/235.1, 236, 435/237, 239, 240.1, 245

[56] References Cited

U.S. PATENT DOCUMENTS 4,235,876 11/1980 Gits et al. .............................. 424/89
4,279,893 7/1981 Kreimer et al. ........................ 424/89

OTHER PUBLICATIONS

*Newcastle Disease in Poultry: a New Food Pellet Vaccine*, Australian Centre for International Agricultural Research, Canberra, 1987, John W. Copland, Ed.

Borland et al., *Biological Abstracts*, vol. 71 (1), Reference #2874, 1980.

Copland, Newcastle Disease in Poultry, a New Food Pellet Vaccine, Australian Center for International Agricultural Research, Canberra, 1987.

*Primary Examiner*—Johnnie R. Brown
*Assistant Examiner*—Abdel A. Mohamed
*Attorney, Agent, or Firm*—Needle & Rosenberg

[57] ABSTRACT

A Newcastle disease vaccine and method of using the vaccine for protecting a poultry animal from Newcastle disease is provided. The vaccine consists of a naturally attenuated live Newcastle disease virus which has the identifying characteristics of ATCC No. VR 2239. The vaccine is capable of conferring solid immunity against Newcastle disease and causes minimal respiratory or other undesirable reactions in inoculated animals.

9 Claims, No Drawings

NATURALLY ATTENUATED NEWCASTLE DISEASE VACCINE AND METHOD OF USING THE SAME

This application was made with support from the United States Department of Agriculture through P.L. 95-113 section 1433 Animal Health and Disease Funds. The United States Government has rights i the invention.

BACKGROUND OF THE INVENTION

The present invention relates to the commercial poultry industry and more particularly to a vaccine against Newcastle disease found in fowl.

Newcastle disease is a viral infection widely distributed throughout the world. The etiologic agent, Newcastle disease virus, is a paramyxovirus of the Family Paramyxoviridae and is classified as serotype I. In general, Newcastle disease is an acute febrile and contagious disease of fowls resembling fowl plague. It is usually characterized by high infectivity with respiratory and nervous symptoms in affected animals. Newcastle disease is transmissible to man, in whom it causes a severe, but transient conjunctivitis. The disease is of particular concern to the commercial poultry industry, in which the economic losses due to livestock morbidity and mortality can be enormous. Several forms of the disease have been identified including velogenic viscerotropic Newcastle disease, velogenic neurotropic Newcastle disease, mesogenic Newcastle disease, and lentogenic Newcastle disease (Beard, C. W. and Hanson, R. P.: Newcastle disease, in *Diseases of Poultry*, 8th Edition, edited by M. S. Hofstad. Iowa State University Press, Ames, Iowa, 1984).

Velogenic viscerotropic Newcastle disease is produced by highly pathogenic strains of Newcastle disease virus and is characterized by high mortality with severe lesions in the gastrointestinal tract. Although present in most other areas of the world, it is not found in the United States. The last outbreak of velogenic viscerotropic Newcastle disease occurred in California during 1970-74 and cost the United States Department of Agriculture (USDA) more than 60 million dollars to eradicate the disease.

Velogenic neurotropic Newcastle disease is also produced by highly pathogenic strains of Newcastle disease virus. This disease is characterized by severe neurological symptoms in infected animals. In most cases, the infected animals do not survive. Velogenic neurotropic Newcastle disease is very seldom seen today in the United States, although it is relatively widespread in other parts of the world.

Mesogenic Newcastle disease is caused by Newcastle disease virus strains that are intermediate in pathogenicity. It is found throughout the world in various fowl.

Lastly, lentogenic Newcastle disease is caused by mildly pathogenic strains of Newcastle disease virus and is characterized mainly by respiratory signs. This form of the disease is quite commonplace in the commercial poultry industry and results in economic losses due to livestock loss, poor livestock growth, feed conversion, and increased livestock carcass condemnation at processing.

In an effort to curtail the economic losses due to Newcastle disease in the commercially poultry industry, young chickens have been routinely vaccinated against the Newcastle disease virus. The vaccines used are prepared with live attenuated Newcastle disease virus derived from lentogenic-type strains and confer immunity against all forms of Newcastle disease.

Chickens are typically inoculated by mass administration procedures including the distribution of the live virus vaccine in drinking water and the spraying of the vaccine directly onto the chickens. In some parts of the world where labor is available and not expensive, chickens are vaccinated with live attenuated emulsified vaccines by injecting each chicken individually. The live virus, once inside the chicken, replicates in the respiratory tract and is spread horizontally from chicken to chicken by aerosol and direct contact routes. Thus, a flock immunity to the various forms of Newcastle disease is established in a relatively short amount of time.

Live virus vaccines have been found to be more desirable than "killed" or inactivated vaccines for use in the commercial poultry industry. A live virus vaccine induces active immunization in a shorter time period than does a "killed" or inactivated vaccine and generally provides both local and durable humoral immunity. The "killed" vaccines require the use of large amounts of antigen to induce immunity, whereas live vaccines are routinely administered in small doses. The "killed" vaccines are also required to be administered parenterally, which is a tedious process. Live vaccines, on the other hand, are easily mass administered by aerosol, spray or drinking water form. Further, live virus vaccines, prepared by growing viruses in cell cultures or chicken embryos, are usually devoid of any potentially allergenic substances, i.e. antibiotics, preservatives, etc., that are sometimes found in "killed" virus preparations.

The use of live virus vaccines in the commercial poultry industry, however, has not been without serious drawbacks. Active immunization with live attenuated vaccines frequently induces a subclinical or mild clinical illness which duplicates, to a limited extent, the disease that is marked for prevention. In the case of chickens inoculated with live attenuated Newcastle disease virus derived from lentogenic-type strains, the replication of the live virus in the respiratory tissues induces a respiratory reaction which is actually a mild form of Newcastle disease.

The respiratory reaction, when uncomplicated, is usually overcome by the natural immunogenic defense mechanisms of the chicken. Both the chicken and the flock will then develop the desired immunity to the Newcastle disease virus. Young chicks have the additional protection of maternal antibodies transmitted from the parent via the yolk sac, and these maternal antibodies decrease, but do not eliminate, the respiratory reaction.

A problem arises, however, when the respiratory reaction becomes complicated due to negative influences found in the chicken breeding environment. These negative influences include the accumulation of dust or ammonia, other concurrent organisms infecting the chickens, and high chicken stocking density. The respiratory reaction in these situations results in severe respiratory symptoms that produce heavy chicken losses even when costly therapy is instituted. Should the chickens not be immediately lost due to illness, the resulting poor growth, feed conversion, and increased carcass condemnation at processing can still add up to a significant economic loss.

Therefore, a need exists for a Newcastle disease virus vaccine of the live attenuated type that is capable of producing solid immunity against all forms of the disease, but that is without the side effects of respiratory or other undesirable reactions in inoculated animals.

Another problem in the present use of live attenuated lentogenic virus strains as vaccines against Newcastle disease is the tendency for the induced flock immunity to be non-uniform and of short duration. This is due primarily to the action of the maternal antibodies found in young chickens of vaccine age. The maternal antibodies tend to neutralize the vaccine virus, ability to replicate and thus prevent the vaccine virus from inducing a solid immunization response. Therefore, there exists a need for a live attenuated Newcastle disease virus vaccine capable of inducing solid immunity in the presence of maternal antibodies.

A further disadvantage of currently used live attenuated lentogenic vaccines is the complicated and costly processing necessary to attenuate the pathogenic virus marked for use as a vaccine. The artificial attenuation is typically accomplished by the passage of the virus through multiple systems (chicken embryos, chicken embryo primary cell cultures, cell lines of different origin, etc.) until an acceptable attenuated virus is obtained. A naturally attenuated lentogenic virus, on the other hand, would be beneficial in eliminating these processing steps and in providing for a more reliable attenuated strain. Therefore, there also exists a need for a live attenuated Newcastle disease virus vaccine that would not require artificial attenuation before use.

A new live attenuated virus used as a Newcastle disease vaccine should also be capable of being administered to chickens in a manner compatible with current mass inoculation procedures. These include inoculating by drinking water and direct spray. Therefore, there exists a further need for a live attenuated Newcastle disease virus vaccine capable of being administered by current mass inoculation techniques.

As a new live attenuated virus vaccine against Newcastle disease must be economically advantageous for use in the commercial poultry industry, the new virus must be capable of being produced in a manner that is cost effective. A virus vaccine that could be produced using already existing commercial virus production technology would be particularly advantageous in keeping production costs down, as much of the set-up and re-tooling costs would be eliminated. The virus vaccine should also have a yield of manufacturing similar to, or greater than, the existing live attenuated vaccine manufacturing method to be economically desirable. Therefore, there exists still a further need for a new live attenuated Newcastle disease virus vaccine capable of being produced using existing commercial virus production technology.

SUMMARY OF THE INVENTION

The present invention relates to the isolation of a naturally attenuated lentogenic Newcastle disease virus and its use as a live Newcastle disease virus vaccine in the commercial poultry industry.

The virus of the present invention is isolated from the intestinal tract of turkeys showing no signs of respiratory disease and is characterized serologically and morphologically as a lentogenic strain of Newcastle disease virus. The isolated virus easily replicates in suitable media and is readily packaged into a live vaccine form. When inoculated into host chickens, a measurable antibody response to the virus vaccine is elicited within one week of inoculation. Solid immunity to Newcastle disease virus is conferred to inoculated chickens as evidenced by resistance to severe Newcastle disease virus challenge.

The virus vaccine of the present invention is found to replicate mainly in the intestinal tract of inoculated chickens where it shows minimal or no tissue damage. Most importantly, the virus is found to be free of any significant respiratory reaction in inoculated hosts.

The virus vaccine of the present invention is capable of inducing solid immunity to Newcastle disease virus with or without the presence of maternal antibodies. The virus vaccine is administered by presently available mass inoculation techniques and is spread horizontally from chicken to chicken. The horizontal spread of the virus vaccine allows for a rapid and uniform inoculation of the flock, which results in a more reliable induced flock immunity. The virus is also naturally attenuated, and therefore does not require the additional processing steps of artificial attenuation. Furthermore, the virus can be produced using already existing commercial virus growing production technology and has similar manufacturing yields.

Although the virus and vaccine of the present invention are demonstrated to immunize chickens, it should be understood that a naturally attenuated lentogenic Newcastle disease virus and live vaccine produced from it are capable of being used in other poultry where Newcastle disease poses a threat. The methods of isolation and use of the virus as a vaccine remain same, regardless of the fowl marked for inoculation.

It is, therefore, an object of the present invention to provide an attenuated live lentogenic Newcastle disease virus for use as a vaccine capable of conferring solid immunity against all forms of the disease.

It is also an object of the present invention to provide an attenuated live lentogenic Newcastle disease virus for use as a vaccine that does not cause a respiratory or other undesirable reaction in inoculated animals.

It is a further object of the present invention to provide an attenuated live lentogenic Newcastle disease virus use as a vaccine that will induce solid immunity in the presence of maternal antibodies.

It is another object of the present invention to provide an attenuated live Newcastle disease virus for use as a vaccine that is capable of being administered by presently used mass inoculation procedures.

It is yet another object of the present invention to provide an attenuated live Newcastle disease virus for use as a vaccine that does not require the artificial attenuation of the live virus before use as a vaccine.

It is still another object of the present invention to provide an attenuated live Newcastle disease virus for use as a vaccine that is produced using already existing commercial virus growing production technology and that has similar yields of manufacturing.

DETAILED DESCRIPTION OF THE PREFERRED EMBODIMENT

In the present invention, a naturally attenuated Newcastle disease virus of the lentogenic type is isolated. The isolated Newcastle disease virus is a paramyxovirus classified as serotype I and belongs to the Family Paramyxoviridae. It contains a single-stranded RNA genome. The isolated virus has been cultured and maintained in a pure form and has been used as a live vaccine against Newcastle disease virus in poultry. The virus has also been deposited with the American Type Culture Collection (ATCC) 12301 Parklawn Drive, Rockville, Maryland on May 9, 1989 and given the number VR 2239.

I. ISOLATION OF A NATURALLY ATTENUATED LENTOGENIC NEWCASTLE DISEASE VIRUS FOUND IN NATURALLY INFECTED FOWL

A. Animal Hosts

The virus of the present invention has been isolated from the intestinal tract of five naturally infected turkeys (Meleagris gallopavo) located in the state of Georgia, U.S.A. The age range of the turkeys was approximately eight to sixteen days old. The selected turkeys showed no clinical signs of Newcastle disease or respiratory illness. Some of the selected turkeys were suffering from a mild intestinal disorder found to be caused by Rotavirus.

B. Method of Isolation

The above-mentioned five turkeys were sacrificed and appropriate intestine and fecal samples obtained. The samples were frozen at approximately −20° C. and stored until processing. The intestine tissue samples were later allowed to thaw and their feca contents expressed and discarded. These intestinal tissues were placed in Tryptose Phosphate Broth (TPB) along with antibiotics (Gentamycin at a concentration of 1.2 mg/ml). The proportion of intestinal material to TPB was approximately 1:5.

The tissues were carefully minced using sterile scissors and forceps and then passed through two layers of gauze and placed in a clean beaker. The sample was then filtered through a paper prefilter to remove most of the tissue debris. The next step was to filter the material through a 0.45 um sterile filter into a sterile vial. The content of this vial was the inoculum used to later inject chicken embryos via the chorioallantoic sac.

Chicken embryos were injected with the above inoculum to propagate the virus of the present invention, thereby enhancing virus replication and providing a greater amount of isolated virus for vaccine use. Other biologic systems that can be used to propagate the virus of the present invention include those well known in the art, such as chicken embryo primary cell cultures and cell lines of various origin.

The isolated virus of the present invention was propagated in the following manner. Approximately 0.1 ml of the above-processed inoculum was inoculated into the chorioallantoic sac of a 9-11 day old specific pathogen free (SPF) chicken embryo. Allantoic fluid was then collected from the embryo approximately 72 hours after inoculation and tested for hemagglutination (HA) activity using a rapid plate test containing approximately 5% chicken erythrocytes. No HA activity was observed at 72 hours. Approximately 0.1 ml of this allantoic fluid was further inoculated into another 9-11 day old SPF chicken embryo and its allantoic fluid tested at approximately 72 hours after inoculation. Again, no HA activity was observed. Approximately 0.1 ml of the allantoic fluid from the second embryo was then inoculated into a third 9-11 day old SPF chicken embryo and, this time, HA activity was detected at 72 hours after inoculation in the allantoic fluid of the third embryo, suggesting virus presence. The allantoic fluid of the third embryo containing the suspected virus was then mixed with anti-Newcastle disease virus antiserum and HA activity was found to be completely inhibited, indicating that the suspected virus was antigenically similar to Newcastle disease virus. The same virus, when mixed with normal (negative) chicken serum, exhibited persistent HA activity.

To discard any possibility of cross contamination in the laboratory, the original intestinal sample was processed in the above manner in a new set of similar SPF chicken embryos. The presence of virus in this series of passages was detected by HA activity and anti-Newcastle disease virus antiserum inhibition after the fourth passage through the embryos.

C. MORPHOLOGIC IDENTIFICATION

The initial isolated virus cultures were tested by electron microscopy for the presence of virus. For observation in the electron microscope, approximately 2 ml of the allantoic fluid containing the virus from the third embryo passage (Section I.B.) was placed in a 15 ml centrifuge tube and centrifuged at approximately 1500 rpm for 30 minutes in a refrigerated (approximately 4° C.) centrifuge (IEC model CRU 5000). The supernatant was collected into another centrifuge tube and the sample recentrifuged at approximately 7000 rpm for 45 minutes in another refrigerated centrifuge (Sorvall model RC2-B). The supernatant was collected again, placed in a 50 ml polystyrene centrifuge tube and centrifuged at 30,000×g for 90 to 120 minutes at 4° C. in an ultracentrifuge (Beckman model L2-65B). The supernatant was discarded and the pellet resuspended in a small amount (less than 0.5 ml) of phosphate buffered saline (PBS). The sample was placed on a carbon coated grid, stained with phosphotungstic acid and observed under the electron microscope. Examination of the sample under the electron microscope revealed pleomorphic particles with a size of approximately 120 nanometers compatible with paramyxovirus.

D. SEROLOGIC ASSAY

Newcastle disease virus, being a paramyxovirus, causes hemagglutination of chicken red blood cells. This hemagglutination is believed to be due to the activity of a surface-projection glycoprotein (HN) found on the virus itself (Murphy, F. A.: Virus Taxonomy, in *Fundamental Virology.* Fields, B. N. and Knipe, D. M. (eds). New York, Raven Press, pp. 18-19, 1986). The hemagglutination (HA) activity can be measured as an indication of viral presence. This is commonly done in a qualitative manner with the rapid plate test as described above.

Hemagglutination (HA) activity can also be utilized in a quantitative manner to represent Newcastle virus infectivity. To find the quantitative hemagglutinating titer of a Newcastle virus, the following general procedure was followed. First, 50 $\mu$l of hemagglutination inhibition (HI) buffer was added to all wells of a "U" or "V" bottom microtiter plate. Then 50 $\mu$l of allantoic fluid containing the isolated virus was added to the first well of the plate. (This was a 1:2 dilution.) A serial dilution was then performed by passing 50 $\mu$l of the solution from each well, starting with the first well, to the next using a microtiter transfer diluter. Then 50 $\mu$l of 0.5% chicken red blood cells (CRBC's) was added to all wells and the plate agitated gently as it stood for 45 minutes at room temperature. A control for the red blood cells was set up by adding 50 $\mu$l of 0.5% CRBC's and 50 $\mu$l HI buffer to a well. After standing at room temperature for 45 minutes, the plate was read to determine the titer of Newcastle virus. The end point (titer)

was determined by noting the highest dilution where there was hemagglutination (no button observed). The control well indicated no hemagglutination (button observed).

Allantoic fluid tested for hemagglutination (HA) activity 72 hours after the first embryo inoculation (See Section I.B.) was found to have a HA titer of 40. After two further passages through SPF embryos (Section I.B.), the HA titer of allantoic fluid had increased to 640. These quantitative levels confirm the results of the rapid plate test in indicating the presence of a HA-producing virus in the isolated samples.

Another serological method utilized in assaying the isolated virus of the present invention was the hemagglutination-inhibition (HI) test in which virus specific HI antibodies are used to detect the presence of a specific virus. Hyperimmune serum containing antibodies against Newcastle disease virus was first obtained from infected chickens. The serum was mixed with a sample of the isolated virus of the present invention (Section I.B.) suspended in a buffer solution. The mixture was then incubated for 20-30 minutes at room temperature. Chicken red blood cells (CRBC) were added to the mixture which was allowed to stand for 45 minutes at room temperature. The mixture was then observed for hemagglutinating activity. No hemagglutination was seen, indicating that the hemagglutinating activity of the isolated virus of the present invention was completely inhibited by hyperimmune serum against Newcastle disease virus.

The hemagglutination-inhibition (HI) test was also used as a serologic assay for the in vivo detection of isolated virus replication in inoculated chickens. The following general procedure was utilized for all HI in vivo tests. Antigen was first diluted in HI buffer to contain 10 hemagglutinating units (HA) in 50 $\mu$l of solution. The antigen solution was then placed into the wells of a "U" or "V" bottom microtiter plate. The first well received 100 $\mu$l of the antigen solution and the remaining wells received 50 $\mu$l of the solution each. Then 25 $\mu$l of serum collected from a chicken was deposited in the first well. The remaining wells were filled using a serial dilution of the mixture in the first well, by passing 50 $\mu$l from it to the next successive well, and so on. The wells were then incubated for 20-30 minutes at room temperature. Approximately 50 $\mu$l of chicken red blood cells (CRBC) (0.5%) was then added to each well. The microtiter plate was agitated gently and allowed to stand for 45 minutes at room temperature. The microtiter plate was then observed and HI titer determined. The end point was taken as the well of the highest serum dilution where no button (positive hemagglutination) was present. This process was repeated for each serum sample obtained from various chickens.

A CRBC control for the HI in vivo test was run by adding 50 $\mu$l of HI buffer and 50 $\mu$l of 0.5% CRBC to a well and observing the expected button (no hemagglutination). An antigen control was also run by first placing 100 $\mu$l of antigen in the first well and 50 $\mu$l of HI buffer in wells #2, 3, 4 and 5. A serial dilution of the antigen control was then performed by transferring 50 $\mu$l from the first well to the next, and so on. Then 50 $\mu$l of 0.5% CRBC was added to all wells and allowed to stand for 45 minutes at room temperature after which the expected buttons (indicating no hemagglutination) were observed.

Sixteen 5-week-old specific pathogen free (SPF) chickens were selected for HI in vivo testing as indicated in Table 1. Chickens designated numbers 1-5 (Table 1) were inoculated by the nasal route using 0.1 ml of inoculum from the third embryo passage (Section I.B.) and were kept in an isolation unit. Chickens designated numbers 6-10 (Table 1) were inoculated by the oral route with the same dosage and inoculum and maintained in another isolation unit. Chickens designated numbers 11-16 (Table 1) were maintained as a control group and left uninoculated in their isolation unit. Three days after inoculation, two of the noninoculated control chickens (numbers 12 and 14, Table 1) were transferred to the same isolation unit occupied by the chickens inoculated by the nasal route. These two chickens were returned to the original control chicken isolation unit after two days of contact with the nasal inoculated chickens. All chickens were then sampled two weeks after inoculation and HI testing performed on their serum as previously described. The HI antibody titer results are shown in Table 1 below.

TABLE 1

| Chicken No. | Route of Inoculation | HI Titer |
| --- | --- | --- |
| 1 | Nasal | 32 |
| 2 | Nasal | 64 |
| 3 | Nasal | 32 |
| 4 | Nasal | 128 |
| 5 | Nasal | 32 |
| 6 | Oral | 16 |
| 7 | Oral | 16 |
| 8 | Oral | 8 |
| 9 | Oral | 32 |
| 10 | Oral | 16 |
| 11 | Control | 8 |
| 12 | Control | 16 |
| 13 | Control | 8 |
| 14 | Control | 16 |
| 15 | Control | 16 |
| 16 | Control | 8 |

Note:
The Group Mean Titer (GMT) for chickens # 1-5 was 57.6; for chickens #6-10 the GMT was 17.6; for chickens # 11-16 the GMT was 12.0.

As shown above, hemagglutination-inhibition (HI) antibody responses were detected in the inoculated chickens, indicating viral replication. There was evidence that the virus spread to noninoculated chickens (numbers 12 and 14) during contact with the nasal inoculated group. There was also evidence that the virus spread within the noninoculated group (chicken number 15), when the two chickens (numbers 12 and 14) placed in brief contact with the nasal inoculated group were reintroduced into the control group isolation unit. These preliminary results indicated that the isolated virus of the present invention spreads from chicken to chicken (horizontally) and by direct contact.

The isolated virus was also assayed utilizing monoclonal antibodies. Using monoclonal antibodies specific for lentogenic strains of Newcastle disease virus, the isolated virus of the present invention was classified as belonging to the lentogenic group of Newcastle disease viruses.

E. NEUTRALIZATION ASSAY

Virus neutralization tests were conducted using SPF chicken embryos and hyperimmune serum. The isolated virus of the present invention (Section I.B.) was mixed in equal amounts with a hyperimmune chicken serum against Newcastle disease virus and allowed to incubate at room temperature for 45 minutes. Serial tenfold dilutions were performed from $10^{-3}$ to $10^{-7}$. Each dilution was inoculated into five 9-10 day old SPF chicken embryos. The embryos were incubated at 37° C. for 7 days. Allantoic fluid was then obtained from each embryo and a plate hemagglutination (HA) test performed. Isolated virus mixed with negative antiserum was prepared in a similar way, except that the dilutions ranged from $10^{-4}$ to $10^{-8}$. The virus and negative antiserum mixture was inoculated into three 9-10 day old SPF chicken embryos per dilution and incubated in the same manner as the virus-hyperimmune serum inoculation described above. At the end of the 7-day incubation, all embryos inoculated with the mixture of virus and hyperimmune serum were negative for HA activity in the rapid plate HA test. All embryos inoculated with the mixture of virus and negative serum were positive for HA activity in the rapid plate HA test after the 7-day incubation. Thus, it was demonstrated that Newcastle disease virus neutralization antibodies were specific for, and neutralized HA activity in, the isolated virus of the present invention.

F. MAINTENANCE OF PURE CULTURE

The isolated virus of the present invention can be maintained in pure culture in specific pathogen free (SPF) chicken embryos or primary cells derived from SPF embryos. The isolated virus was adapted to grow in SPF chicken embryo kidney cells in an effort to clone it. Successful cloning has been demonstrated in chicken embryo kidney cells that yielded plaques of several sizes.

The SPF chicken embryo kidney cells were prepared for culturing in the following manner. Kidneys were removed from 17–20day old chicken embryos under sterile conditions and placed into a glass beaker containing phosphate buffer solution (PBS) without calcium or magnesium (Modified PBS) or Hank's balanced salt solution (HBSS) without calcium or magnesium. The supernatant of the mixture was poured off and kidneys then cleaned and washed 3–4 times with Modified PBS or HBSS without calcium or magnesium. Any large tissue chunks were minced lightly with scissors or squeezed gently with forceps. The last wash was drained off and tissue fragments poured into a trypsinization flask containing a magnetic stir bar. Approximately 50–100 ml of prewarmed (37° C.) trypsin-EDTA solution was added to the flask and the solution stirred very slowly for 15–20 minutes on a stirrer base in a 37° C. incubator. When the supernatant became cloudy, the stirring was stopped and the flask shaken before it was set down for several minutes to let the clumps settle out. The supernatant was placed on a glass slide and observed for the proper cell density. The supernatant was then filtered through a gauze-covered funnel into a sterile graduated centrifuge tube with 5 ml of cold heat-inactivated calf serum in it which was used to stop the trypsin action. This process was repeated 1–2 times, each time the process lasting approximately 10 minutes. Total trypsinization time was held under one hour. The mixture was then centrifuged at 1000 RPM for 10 minutes by which time the kidney cells (and RBC's) had formed a pellet. The trypsin solution was then poured off, tested for sterility, and discarded. The obtained cells were resuspended in minimal essential medium (MEM) or Hams F-10 with Earle's balanced salt solution (EBSS) and 10% heat-inactivated fetal calf serum then added. Approximately one ml of cell pack was resuspended in approximately 200 ml of MEM or Hams F-10 with EBSS. Cells were counted in a hemocytometer by resuspending them in a known amount of media. A 1:10 dilution of cells was then made in trypan blue. Cells were plated out in 35 $mm^2$ plates containing appropriate media and incubated. A concentration of approximately $2.5\times10^6$ cells per ml of media was used.

Once the cell monolayer was formed in the 35 $mm^2$ plates (approximately 24 hours), the virus present in the allantoic fluid of the third embryo passage (See Section I.B.) was inoculated into the plates (approximately 0.1 ml of allantoic fluid inoculum per plate) and allowed to attach for a period of approximately 45 minutes. Two milliliters of maintenance cell culture medium (Earle's minimal essential medium) with 2% calf serum was added and the cultures observed daily for the presence of cytopathogenic effect (CPE). After 4 days of incubation, the cells were freeze-thawed three times, centrifuged to discard the pellet, and the supernatant reinoculated in new monolayers. CPE was observed after the second passage, although it was more evident and abundant after the third passage.

The virus has also been "purified" by dilution to extinction and stable seeds produced. The virus has not been inoculated into cell lines yet, although this is certainly possible.

The embryo infective dose ($EID_{50}$) has been found to be between $10^{-8.5}$ to $10^{-9.5}$ per ml. No mortality in embryos was seen during the first 96 hours. At lower dilutions some mortality was observed after the 5th day post-inoculation.

II. USE OF THE ISOLATED VIRUS AS A LIVE ATTENUATED NEWCASTLE DISEASE VIRUS VACCINE

A. Animals

The isolated lentogenic Newcastle disease virus of the present invention has been used as a live attenuated vaccine against Newcastle disease virus in chickens. The vaccine is also capable of being employed as a vaccine in other poultry where Newcastle disease infection is of concern, as the method of virus isolation and vaccine use would be the same regardless of the type of fowl targeted for immunization.

A selection of 120 broiler chickens was made for vaccine inoculation. The healthy animals were selected from a broiler company located in Athens, Georgia and were presumed to be free of any other infectious diseases at the time of immunization.

B. ROUTE OF VACCINE ADMINISTRATION

The live attenuated vaccine of the present invention may be administered to poultry animals by a number of commonly used inoculation techniques. These include direct spray, ocular, drinking water, and parenteral routes. Of these, the direct spray, ocular, and drinking water routes are the most commonly used techniques in mass inoculation environments and were the route chosen for the following experimental inoculations.

The vaccine of the present invention is prepared without elaborate processing steps. In general, the virus of the present invention is first isolated or obtained from a poultry animal (Section I.B.) or from a virus culture (i.e., ATCC No. VR 2239). The isolated or obtained virus is then propagated in a biologic system to secure an effective amount of virus to immunize a poultry animal. As previously mentioned, various biologic systems well known in the art (i.e., chicken embryos, chicken embryo cell cultures, cell lines) can be utilized in propagating the virus. The propagated virus may then be inoculated directly into a poultry animal as a live virus vaccine. The virus vaccine may also be placed or incorporated in a carrier, such as water, before inoculation into the poultry animal. The carrier allows for the uniform dispersion of the virus vaccine during inoculation and for the precise dilution of the virus, if necessary. The carrier is selected so as not to be detrimental to the virus vaccine in any way.

The isolated virus of the present invention was prepared for administration as a vaccine via the direct spray route in the following manner. Approximately 2 ml of allantoic fluid from a third embryo passage (Section I.B.) containing the isolated virus having the identifying characteristics of ATCC No. VR 2239 was placed into 360 ml of distilled water and introduced into a commercially available spray vaccinator such as the type available from the Intervet Company, Boxmeer, Holland. The chickens were exposed to the spray emanating from the vaccinator for approximately two seconds. This resulted in a virus dosage of approximately $6.5 \times 10_{50}$ per chicken. Two groups of 20 one-day old chickens each were vaccinated by this method (See Table 2, Groups II, III).

Two other groups of 20 chickens each were vaccinated via the ocular route with a vaccine prepared by diluting 1 ml of the allantoic fluid obtained from the third embryo passage (Section I.B.) in 30 ml of sterile distilled water (Table 2, Groups IV, V). Each chicken received one drop of the diluted virus solution at one day of age. The approximate virus dosage administered to each chicken in this manner was $9.58 \times 10^{7.0}$ EID$_{50}$.

Another group of 20 chickens was left uninoculated to serve as the control group in these experiments (Table 2, Group VI).

At 17 days of age, one group of chickens from the spray-inoculated groups (Table 2, Group III) and one group of chickens from the ocular-inoculated groups (Table 2, Group V) were revaccinated with the virus vaccine via drinking water. In addition, a new group of previously non-vaccinated chickens (Table 2, Group I) was administered the vaccine via drinking water at 17 days of age. The drinking water inoculum was prepared by mixing approximately 1.0 ml of the allantoic fluid from the third embryo passage (Section I.B.) with a powdered milk solution comprising 9.0 grams of powdered milk per 3 liters of water. This resulted in a virus inoculum of approximately $1.05 \times 10^4$ EID$_{50}$ per milliliter of solution. Approximately 30-35 ml of this mixture was administered via drinking water to each chicken of the above-described three groups, resulting in a final virus dosage of approximately 3.0 to $3.5 \times 10^5$ EID$_{50}$ per chicken.

Blood specimens were obtained from a sampling of 10 chickens from each group of 20 chickens at 1, 14, 24, and 34 days of age. The samples were tested for the presence of HI antibodies.

At 34 days of age, 10 chickens from each group were taken to the isolation units of the Poultry Disease Research Center and challenged with the Texas GB strain of Newcastle disease, a velogenic strain. Each chicken was challenged with $10^{4.0}$ EID$_{50}$ of virus given by the intramuscular route. Chickens were observed for one week, keeping records of mortality and clinical signs. At 40 days of age, blood samples were obtained from all challenged the chickens and tested for the presence of HI antibodies.

C. RESULTS

The results of the experimental inoculation with the virus vaccine of the present invention are summarized in Table 2 below. The shown titers of hemagglutination-inhibition (HI) antibodies specific to Newcastle disease virus are the average titers for a sample of 10 birds from each group of 20 birds at 1, 14, 24, and 34 of age. The hemagglutination-inhibition (HI) titers at 40 days of age are shown for the challenged chickens (10 birds from each group). The percent mortality figures represent the average mortality obtained in the challenged birds after one week following the velogenic strain challenge.

TABLE 2

| GROUP NUMBER | VACCINATION ROUTE | AGE (DAYS) | HI ANTIBODY TITERS AGE (DAYS) | | | | | PERCENT MORTALITY** |
|---|---|---|---|---|---|---|---|---|
| | | | 1 | 14 | 24 | 34* | 40** | |
| I | DRINKING WATER | 17 | 73 | 6 | 4 | 15 | 79 | 0 |
| II | DIRECT SPRAY | 1 | 73 | 5 | 6 | 8 | 156 | 40 |
| III | DIRECT SPRAY AND DRINKING WATER | 1 17 | 73 | 12 | 3 | 12 | 76 | 20 |
| IV | OCULAR | 1 | 73 | 11 | 5 | 1 | 255 | 80 |
| V | OCULAR AND DRINKING WATER | 1 17 | 73 | 5 | 3 | 11 | 200 | 10 |
| VI | NON-VACCINATED CONTROL | | 73 | 6 | 4 | 1 | 256 | 90 |

*PRECHALLENGE
**POSTCHALLENGE

The HI antibody titers obtained for all chicken groups at one day of age represent a maternal antibody titer and are considered to be very high. At 34 days of age, the HI antibody titers were highest in those chickens vaccinated or revaccinated at 17 days of age via drinking water (Groups I, III, V). Chickens vaccinated only at one day of age (Groups II, IV) had lower HI antibody titers at 34 days of age, most likely due to the high level of maternal antibodies still present at one day of age. As expected, the non-vaccinated control group (Group VI) exhibited the lowest HI antibody titers over the 34-day period.

After challenge with the velogenic strain of Newcastle disease virus, the highest percentage of survivors was observed in the groups of chickens vaccinated or revaccinated at 17 days of age via drinking water (Groups I, III, V). The chicken groups receiving the vaccine only at one day of age (Groups II, IV) experienced the highest mortality of all vaccinated groups. The non-vaccinated control group (Group VI) experienced the overall highest mortality (90%) of all group in the study.

No respiratory reaction following vaccination was observed in any of the experimental chicken groups which were all maintained in floor pens.

D. CONCLUSIONS

It has been found that a newly isolated lentogenic Newcastle disease virus can be effectively used as a live vaccine against Newcastle disease in chickens. The novel virus induces a solid immunity in inoculated hosts without the side effects of respiratory or other undesirable reactions found in currently used live attenuated Newcastle disease virus vaccines. The new virus vaccine, being naturally attenuated, is easy to manufacture and can be administered with current mass inoculation techniques. Although initially tested in chickens, the live virus vaccine is capable of being used against Newcastle disease in other poultry, as the method of isolation and use of the vaccine would be the same.

What is claimed is:

1. A method of protecting a poultry animal from Newcastle disease, comprising the step of administering to said animal an effective amount of a live naturally attenuated non-pathogenic Newcastle disease virus to cause immunization in said animal, wherein said Newcastle disease virus is the same virus originally isolated from the intenstine of healthy turkey and replicates primarily in the digestive tract and the virus is the same virus contained in ATCC No. VR 2239.

2. The method of claim 1, and further comprising the step of incorporating said virus in a carrier prior to said administering step.

3. The method of claim 1, wherein said administering step comprises distributing said virus in the drinking water of said animal.

4. The method of claim 1, wherein said administering step comprises spraying said animal with said virus.

5. The method of claim 1, wherein said administering step comprises inoculating said animal with said virus by the ocular route.

6. The method of claim 1, wherein said administering step comprises inoculating said animal with said virus by the parenteral route.

7. A vaccine for the prevention of Newcastle disease in poultry comprising an effective immunizing amount of a live naturally attenuated non-pathogenic Newcastle disease virus, wherein said Newcastle disease virus is the same virus originally isolated from the intestine or healthy turkey and replicates primarily in the digestive tract and the virus is the same virus contained in ATCC No. VR 2239.

8. The vaccine of claim 7, and further comprising a carrier for said virus.

9. The vaccine of claim 8, wherein said carrier is water.

* * * * *